Figure 1:
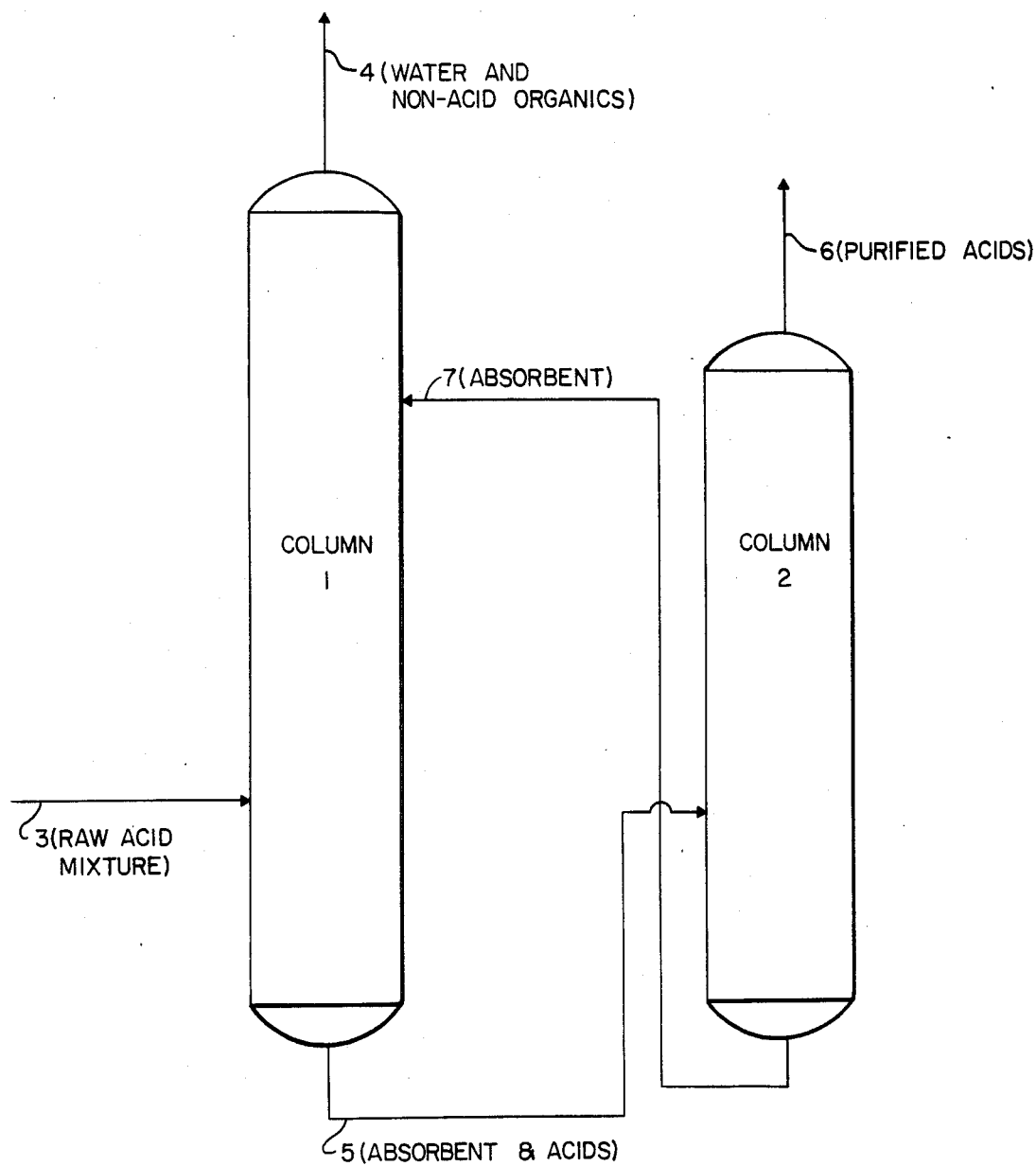

United States Patent [19]

Cohen

[11] Patent Number: 4,576,683

[45] Date of Patent: Mar. 18, 1986

[54] METHOD FOR SEPARATING CARBOXYLIC ACIDS FROM MIXTURES WITH NON-ACIDS

[75] Inventor: Lester R. Cohen, The Woodlands, Tex.

[73] Assignee: Badger B.V., The Hague, Netherlands

[21] Appl. No.: 617,701

[22] Filed: Jun. 6, 1984

Related U.S. Application Data

[63] Continuation-in-part of Ser. No. 399,717, Jul. 19, 1982, abandoned.

[30] Foreign Application Priority Data

Jul. 24, 1981 [NL] Netherlands ............... 8103517

[51] Int. Cl.⁴ .................. C07C 51/44; B01D 3/40
[52] U.S. Cl. .................... 203/15; 203/16; 203/58; 203/60; 203/38; 203/DIG. 21; 203/78; 203/84; 562/600; 562/606; 562/608
[58] Field of Search .............. 203/58, 15, 16, 60, 203/59, DIG. 21, 78, 84, 38; 562/607–609, 600

[56] References Cited

U.S. PATENT DOCUMENTS

| | | | |
|---|---|---|---|
| 1,795,977 | 3/1931 | Suida ............................ | 203/16 |
| 3,478,093 | 11/1969 | Nonnenmacher et al. ......... | 562/600 |
| 3,878,241 | 4/1975 | Muller ............................ | 203/16 |
| 3,951,755 | 4/1976 | Sartorius et al. ................ | 203/16 |
| 4,076,594 | 2/1978 | Buelow et al. .................. | 203/15 |
| 4,217,460 | 8/1980 | Hohenschutz et al. .......... | 562/608 |
| 4,262,140 | 4/1981 | Bott et al. ...................... | 203/15 |
| 4,326,073 | 4/1982 | Wolf et al. ..................... | 562/609 |

FOREIGN PATENT DOCUMENTS

0120537 9/1980 Japan ..................... 203/58

*Primary Examiner*—Wilbur Bascomb
*Attorney, Agent, or Firm*—Schiller & Pandiscio

[57] ABSTRACT

A method for separating carboxylic acids from mixtures with non-acids by an extractive distillation method using a lactam with a 5- or 6-membered ring, preferably N-methyl-2-pyrrolidone, as an extractant to extract the acids from the mixture with non-acids, followed by separating the extracted acids from the extractant by rectification.

19 Claims, 1 Drawing Figure

METHOD FOR SEPARATING CARBOXYLIC ACIDS FROM MIXTURES WITH NON-ACIDS

This is a continuation-in-part of my copending application Ser. No. 399,717, filed July 19, 1982, and now abandoned.

The invention relates to a method for separating carboxylic acids from mixtures with non-acids by an extractive distillation treatment using an amide as a solvent, i.e., as the extractant, followed by separating the acids from the solvent.

For many years it has been known to separate carboxylic acids from mixtures with non-acids using tertiary amines as a solvent. Thus, von Garwin in Ind. Eng. Chem., vol. 45, page 1558 (1953) suggested the use of dimethylaniline for the recovery of acetic acid from aqueous mixtures of said acid. Dimethylaniline, however, has the disadvantage of forming an azeotrope which must be separated at substantial cost.

In U.S. Pat. No. 3,878,241 it has been proposed to use 1,2-dimorpholinoethane (DMPE) as the solvent for the separation of acetic acid from aqueous mixtures. DMPE has the advantage over dimethylaniline in that it does not form a minimum azeotrope with water, which makes the separation and recovery of the acetic acid and of further acids which are present in the acids containing mixture, easy. It further gives no problems with other water miscible low boiling point materials, such as lower alcohols, ketones and esters, which may be present in the acids containing mixture.

However, DMPE also has certain drawbacks. DMPE is not completely stable at higher temperatures: in view of this the conditions in the extraction distillation and solvent recovery steps must be restricted to working at rather low temperature, which means working at low pressures in the column. Thus, the pressure at the head of the extraction column must be between 0.133 bar and 1.33 bar and preferably less than 1 bar, while in the examples pressures at the head of this column have been applied of 0.5 bar. The pressure at the head of the acid recovery column is generally between about 0.027 and 0.27 bar and preferably between 0.07 and 0.20 bar. Especially for separating and recovering formic acid from mixtures with non-acids the pressures should be low, as it decomposes at 200° C. These low pressures require large columns with provisions for maintaining the desired vacuum and the vapors formed are of low density and require large condensers. Further DMPE has a rather high melting point of about 75° C. which complicates its applicability; to be suitable as an absorbent it must be in liquid form, i.e. at temperatures above the melting point. Finally, 1,2-dimorpholinoethane is not readily available and must be especially prepared from morpholine and 1,2-dichloroethane, e.g. in a similar way as disclosed in DE-B No. 1 111 189 and in Chemical Abstracts vol. 56, page 8531 (1962) which makes its application on a technical scale unattractive.

Because of these disadvantages and drawbacks of the tertiary amines, it has been proposed to use instead certain amides as the solvent in an extraction distillation treatment for separating carboxylic acids from mixtures with non-acids.

Thus, in DE-A No. 2 408 011 it is proposed to use N-methylacetamide in such a process instead of DMPE. However, this compound has a melting point of 28° C. and in order to reduce this it is proposed to add water to the recirculated absorbent. Moreover in the process according to this patent application there is worked at low pressure and with a high reflux ratio, which means that the column in question has large dimensions and is complicated.

In DE-A No. 2 545 730 it is proposed to use N-formyl morpholine as a solvent for recovering formic acid from mixtures with non-acids. Also here there should be worked under an unreasonably high vacuum to separate the acid from the absorbent.

Now, it has been found that these drawbacks do not exist and moreover a better efficiency is reached if, and the method of the invention is characterized in that, as the absorbent is used a lactam which is liquid at ambient temperature and under the process conditions is miscible in all proportions with the mixture of acids and non-acids, so that always only one liquid phase exists.

It is observed that from U.S. Pat. No. 3,478,093 it is known to apply lactams having a 4–7 membered ring and bearing a hydrocarbon group on the N-atom, which if desired are further substituted by hydrocarbon groups on one or more carbon atoms in the ring (particularly 2-pyrrolidones which have been substituted on the N-atom by an alkyl group) for the extraction of (meth)acrylic acid from liquid or vaporous mixtures of these acids and non-acids, especially aqueous mixtures. However, the disclosure of this patent is exclusively directed towards extraction (a process where two separate liquid phases prevail) and thus to the use of lactams which are substantially immiscible with the acid containing mixtures.

Thus, for the extraction of aqueous (meth)acrylic acid solutions, this patent requires the use of lactams having extremely low water solubility of up to about 0.2% by weight.

DE-A No. 2 545 658 describes the use of secondary amides, which are practically water immiscible for the extraction of acetic, propionic and/or acrylic acid from aqueous mixtures, followed by distillation of the extract to recover the acids.

For use in the method of the invention the lower lactams with a 5 or 6 membered ring are particularly suitable for the separation of carboxylic acids from aqueous mixtures. Of these lactams N-methyl-2-pyrrolidone (NMP) is especially preferred. It is readily available on the market and has very attractive properties viz: completely miscible with water and organic (polar) solvents, molecular weight 99.1; freezing point $-24.4$ C.°; boiling point (1 bar) 202° C.; specific gravity (25° C.) 1027 kg/m$^3$; viscosity (25° C.) 1.65 cP; surface tension (25° C.) $40.7 \times 10^{-3}$ N/m; spec. heat (20° C.) 1.67 J/g; heat of vaporization 533 J/g; flash point (open cup) 95° C.; low toxicity, LD$_{50}$ (rats) 7 g/kg, no azeotrope with water (vide the book "m-Pyrol", N-methyl-2-pyrrolidone, Ed. GAF, 1972) stable at temperatures up to about 425° C. and biodegradable, which make it especially suitable for the extraction and recovery steps. It forms adducts with the acids which adducts can be decomposed by a suitable combination of temperature and pressure.

The method of the invention is not restricted to the separation and recovery of a specific acid as is the case with the method disclosed in the above-mentioned U.S. Pat. No. 3 878 241, DE-A No. 2 408 011 and DE-A No. 2 545 730 but is generally applicable for the separation and recovery of C$_{1-10}$ aliphatic and/or C$_{3-10}$ olefinic carboxylic acids from mixtures with non-acids.

These acids comprise lower alkanoic acids, such as formic acid, acetic acid, propionic acid, and the butyric acids, which are e.g. obtained by direct oxidation of light petroleum fractions from refineries, largely consisting of propane and butane, according to the Celanese and B.P. processes (Kirk and Othmer, Encyclopedia of Chemical Technology, second ed., vol. 8 pages 396–397 (1965), and unsaturated monocarboxylic acids such as acrylic acid and methacrylic acid.

The mixtures wherein the acids are present and from which they are to be separated and recovered may e.g. be solutions in polar solvents, such as aqueous mixtures, which may further contain various contaminants or mixtures with other oxygenated hydrocarbon compounds e.g. mixtures with alcohols, aldehydes, and/or ketones, which also may contain further contaminants, such as effluents from the oxidation reactions and for preparing alkanoic acids.

The method of the invention can particularly suitably be applied on aqueous mixtures of formic, acetic and/or propionic acid, which mixtures further generally contain unconverted hydrocarbons (propane, butane) and other oxygenated compounds, and on mixtures which comprise (meth)-acrylic acid. These mixtures can e.g. be the mixtures which are obtained by condensation of the oxidation reactor effluent followed by flashing the light fraction ($H_2O$, unconverted hydrocarbons) or preferably the vapor phase which remains when quenching and separating heavy ends from the effluent of the oxidation reactor. Such a vaporous phase is preferred because it saves heat.

The conditions used in the extraction and recovery steps can be chosen, according to normal engineering practice.

The proportion of lactam (preferably NMP) used in the process is dependent upon the amount of acid to be separated and recovered from the mixture. If all available acid should be recovered then 1 mole equivalent NMP should be used for each equivalent of acid groups. In practice one may use less or more, e.g., 1.2 to 2 equivalents of NMP for each equivalent of acid groups to be recovered. The extraction can if desired be carried out at elevated pressure. Especially when the acid containing mixture is available as a vaporous phase under pressure, it may be advantageous to conduct the extraction of the mixture at that pressure and to strip light impurities under lower pressure. The stripping is preferably carried out under a pressure in the stripping section of column 1 of 0.5 to 2 bars and in particular of about 1 bar. Under these conditions the stripping proceeds properly and the column can be of simple construction.

The conditions in the recovery step are determined by the acid which has been extracted. For, the acid-lactam adduct which is formed in the extraction stripping step must be decomposed in the recovery step and this requires that the temperature in the recovery step is at least equal to the temperature at which the adduct decomposes. This minimum temperature varies with the acid in question.

Thus, the pressure under which the recovery column works i.e. the pressure at the head of the recovery column must be at least so high that in the column the required temperature for decomposition of the adduct is reached, but not so high that decomposition of the acid(s) occurs. Especially formic acid is very sensitive to decomposition.

In practice the pressure which is applied depends on economic considerations and on the product which is desired.

Whether the acid is recovered as top product or as bottom product depends on the type of acid and on the lactam which is used. Acids which at the pressure applied have a lower boiling point than said lactam (for NMP this is e.g. the case with formic, acetic, acrylic and methacrylic acid) are obtained as top procuct. Acids which at the pressure applied have a higher boiling point than the lactam are obtained as bottom product.

The type of column to be used for both steps is not important. One can suitably use any type of tray column or packed column.

The invention is now further described and elucidated by means of the drawing, which shows a simplified flow sheet of an extractive distillation and recovery system for carrying out the present invention, which is only an example of the way wherein the method of the invention can be carried out. Instead of course also other standard systems for absorption-stripping and recovery of the product can be applied.

The system shown in the drawing comprises an extraction distillation column 1 and a distillation-type recovery column 2, both of which are provided with the usual heating (reboiler) sections, condensers for distillate and reflux systems (not shown).

The acid containing mixture enters column 1 at an intermediate point 3. This feed can be introduced in liquid form, vapor form or mixed liquid and vapor form depending on the form wherein this feed is available. Vapor of this feed rises to the top of the column. The solvent (sometimes called "extractant") is introduced in liquid form in the upper part of the column at 7. The solvent flows down the column and extracts the acid from the feed. The substances with which the acid in the feed was contaminated leave the top of the column 1 at 4 in vapor form and are condensed. If this is practical, part of this condensate may be returned as reflux.

A mixture of acid and solvent (adduct plus free solvent) leaves the bottom of column 1 at 5. This mixture is introduced into the recovery column 2. Herein the acid is separated from the mixture as top product 6. The solvent is recovered as bottom product and is recycled to and introduced into column 1 at 7.

The process of the invention is further elucidated by the example. In the example all percentages and parts are by weight, unless otherwise stated.

The tests described in the examples were carried out in an extractive distillation and rectification system as shown in the FIGURE. The various compositions indicated in the examples are in percent by weight.

EXAMPLE I

Column 1 of the extractive distillation and rectification system comprised 55 practical plates and worked under atmospheric pressure at the head of the column; column 2 comprised 60 practical plates and worked under a pressure of about 0.3 bar at the head of the column.

Via line 3 a mixture of 64.7% of acetic acid, 5.5% of formic acid, 2% light ends and 27.8% of water having a temperature of 115° C. (100% vapour form) was introduced on the 20th plate (calculated from the bottom) of column 1, and on the 40% th plate (calculated from the bottom) was continuously introduced via line 7 an absorbent mixture comprising 4.7% of acetic acid, 0.4% of formic acid, less than 0.1% of water and 94.9% of NMP in an amount of 2 parts by weight per part by weight of feed introduced via line 3. The liquid which flowed down in column 1 and was collected in the bottom section was heated to boiling.

Under these conditions and with a reflux ratio of 0.5, the temperature at the head of the column was substantially 100° C. and a top product was obtained from line 4 comprising acetic acid less than 0.1%, formic acid less than 0.1%, water and light ends. The bottom product from this column 1 comprised acetic acid 28.6%, formic acid 2.0%, water 0.1% and NMP 69.6%.

The bottom product from column 1 was continuously passed via line 5 to the rectification column 2 and was introduced on the 40th plate (calculated from the bottom). By heating the bottom product to boiling and using a reflux ratio of 1,0 a top product was obtained from line 6, which comprised acetic acid 92.0% formic acid 7.6% and water 0.4%. The bottom product comprised acetic acid 4.7% formic acid 0.4%, water 0.1%, and NMP 94.9%. This bottom product was used as the extractant or solvent mixture in the extractive distillation and passed to column 1 via line 7.

EXAMPLE II

The process of example I was repeated using the same apparatus and working under the same pressures and with the same reflux ratios.

The mixture introduced via line 3 now comprised 66.2% of acetic acid; 5.7% of formic acid; less than 2% of light ends and 26.1% of water and was 100% vapour form.

The solvent rich mixture introduced via line 7 comprised 3.1% of acetic acid; 0.5% of formic acid, less than 0.1% of water and about 96.4% of NMP and was used in an amount of 1.6 parts by weight per part by weight of feed introduced via line 3.

The top product obtained from line 4 consisted of water and light ends; acetic acid and formic acid were not detectable.

The bottom product from column 1 comprised acetic acid 30.2%, formic acid 2.8%, water less than 0.1%; NMP 66.9%.

The top product obtained from column 2 via line 6 comprised acetic acid 91.8%; formic acid 7.9%; water 0.3%.

The bottom product from column 2 had the composition indicated herein before for the solvent rich stream via line 7. This example shows that under optimum conditions substantially 100% of the acids can be recovered as a concentrated product.

EXAMPLE III

The same apparatus as was used in Examples I and II was applied for the separation of methacrylic acid from an aqueous mixture.

The working conditions were as follows:

|  | Column 1 | Column 2 |
|---|---|---|
| reflux ratio | 1 | 2 |
| pressure at head of column | 0.4 bar | 0.4 bar |
| temperature at head of column | 175° C. | 182° C. |
| temperature at bottom of column | 77° C. | 133° C. |

Composition of streams introduced into and withdrawn from columns

|  |  |  |
|---|---|---|
| | Column 1 | |
| feed introduced through line 3 | 50% methacrylic acid 50% water | |
| extractant stream through line 7 | methacrylic acid | 26.8% |
| | water | 0.1% |
| | NMP | 73.1% |
| stream through line 4 | methacrylic acid | 9.17% |
| | water | 90.8% |
| bottom product | methacrylic acid | 44.86% |
| | NMP | 54.94% |
| | water | 0.2% |
| | Column 2 | |
| feed | bottom product from column 1 | |
| stream through line 6 | methacrylic acid | 99.15% |
| | water | 0.62% |
| | NMP | rest |
| bottom product | has composition of the extractant stream passed via line 7 to column 1. | |

The apparatus used in this example does not give an optimum result; nevertheless this example shows that even under non-optimum conditions a good recovery of methacrylic acid is obtained.

In the practice of this invention it is preferred that the lactam be an unsubstituted pyrrolidone or a $C_1$–$C_4$ N-substituted pyrrolidone, e.g., N-methyl-2-pyrrolidone (which is especially preferred and constitutes the preferred embodiment of the invention), N-isopropyl pyrrolidone (NIPP), and 2-pyrrolidone. The 2-pyrrolidone and NIPP have properties close to NMP, as seen by Table I.

TABLE I

|  | NMP | NIPP | 2-Pyrrolidone |
|---|---|---|---|
| Atmospheric boiling point °C. | 202 | 216 | 250 |
| Formula weight | 99 | 127 | 85 |
| Heat of Vaporization (J/G) | 533 | 386 | 620 |
| Solidification Point °C. | −24.4 | 18 | 25 |

Table II illustrates how the invention may be practiced using NIPP and 2-pyrrolidone in place of NMP. Examples IIA and IIB in Table I illustrate the effects of replacing NMP with NIPP and 2-pyrrolidone respectively. Examples IIA and IIB repeat the process of Example II, using the same feed and apparatus as Example II. For convenience of comparison, Table II also sets forth the corresponding data for Example II.

TABLE II

| Example | II | II-A | II-B |
|---|---|---|---|
| Column I conditions: | | | |
| Operating pressure | atm | same | same |
| Reflux ratio | 0.5 | same | same |
| Weight ratio solvent/feed | 1.6 | 2.0 | 1.4 |
| Acid content in top | Negl. | Negl. | Negl. |
| Bottom composition: | | | |
| wt % acetic acid | 30.2 | 25.8 | 31.6 |
| wt % formic acid | 2.8 | 2.4 | 2.8 |
| wt % water | <0.1 | <0.1 | <0.1 |
| wt % pyrrolidone | 66.9 | 71.7 | 65.5 |
| Column II conditions: | | | |
| Operating pressure bar abs | 0.3 | 0.2 | 0.1 |
| Reflux ratio | 1.0 | 0.5 | 0.1 |
| Top composition: | | | |
| wt % acetic acid | 91.8 | same | same |
| wt % formic acid | 7.9 | same | same |
| wt % water | 0.3 | same | same |
| Bottom composition: | | | |

TABLE II-continued

| Example | II | II-A | II-B |
|---|---|---|---|
| wt % acetic acid | 3.1 | 2.4 | 0.4 |
| wt % formic acid | 0.5 | 0.4 | 0.1 |
| wt % water | 0.1 | Negl. | Negl. |
| wt % pyrrolidone | 96.3 | 97.2 | 99.5 |

It is to be noted that the specific compounds identified in Table II above all have a boiling point of 260° C. or less and consist of 4–7 total carbon atoms.

We claim:

1. A method for separating $C_1$–$C_{10}$ aliphatic and $C_3$–$C_{10}$ olefinic carboxylic acids from mixtures with non-acids comprising an extractive distillation treatment, using an amide as an extractant, to recover an extractant-acid mixture followed by recovery of the acids from the extractant-acid mixture by rectification, characterized in that the amide extractant used in the extractive distillation treatment is a lactam from the group consisting of lactams having a 5-membered ring and lactams having a 6-membered ring, said lactam being a liquid at ambient temperature and being miscible in all proportions under the process conditions with the mixture of acids and non-acids.

2. A method according to claim 1 wherein said lactam is a pyrrolidone having a boiling point less than 260 degrees C.

3. A method according to claim 2 wherein said lactam has a total of 4 to 7 carbon atoms.

4. A method according to claim 3 wherein said lactam is a member of the group consisting of N-methyl-2-pyrrolidone, 2-pyrrolidone, and N-isopropyl-pyrrolidone.

5. A method according to claim 4 wherein the extractant is N-methyl-2-pyrrolidone.

6. A method according to claim 4 wherein the extractant is N-isopropyl pyrrolidone.

7. A method according to claim 4 wherein the extractant is 2-pyrrolidone.

8. A method according to claim 1 wherein the mixture comprises a member of the group consisting of acrylic acid and methacrylic acid.

9. A method according to claim 8 wherein the extractive distillation is carried out under a pressure of 0.5 to 2 bars absolute.

10. A method according to claim 1 wherein the lactam comprises a 6-membered ring.

11. A method for separating $C_1$–$C_{10}$ aliphatic carboxylic acids and $C_3$–$C_{10}$ olefinic carboxylic acids from mixtures with non-acids by extractive distillation, comprising the steps of:

submitting a mixture of (a) at least one non-acid component and (b) at least one acid from the group consisting of $C_1$–$C_{10}$ aliphatic carboxylic acids and $C_3$–$C_{10}$ olefinic carboxylic acids to extractive distillation with a lactam from the group consisting of lactams having a 5-membered ring and lactams having a 6-membered ring, said lactam being liquid at ambient temperature and miscible in all proportions with said mixture;

recovering from said extractive distillation a mixture comprising said at least one acid and said lactam; and subjecting said mixture to distillation so as to separate said at least one acid from said lactam by rectification.

12. A method according to claim 11 wherein said lactam comprises (a) a heterocyclic ring containing only carbon and nitrogen atoms and (b) an amide oxygen directly attached to a carbon atom in said ring.

13. A method according to claim 12 wherein said lactam comprises a 5-membered ring.

14. A method according to claim 13 wherein said lactam is N-methyl pyrrolidone, N-isopropyl-pyrrolidone, or 2-pyrrolidone.

15. A method according to claim 14 wherein said lactam comprises a 6-membered ring.

16. A method according to claim 1 wherein said lactam is an alkyl N-substituted pyrrolidone.

17. A method according to claim 11 wherein said mixture of at least one non-acid component and at least one acid is aqueous.

18. A method for separating $C_1$–$C_{10}$ aliphatic carboxylic acids and $C_3$–$C_{10}$ olefinic carboxylic acids from mixtures with non-acids by extractive distillation, comprising the steps of:

passing into a first distillation column a mixture of (a) at least one non-acid component and (b) at least one acid from the group consisting of $C_1$–$C_{10}$ aliphatic carboxylic acids and $C_3$–$C_{10}$ olefinic carboxylic acids, passing into said first distillation column a lactam from the group consisting of lactams having a 5-membered ring and lactams having a 6-membered ring, said lactam being liquid at ambient temperature and miscible in all proportions with said mixture, contacting said mixture with said lactam in said first distillation column so that said at least one acid is extracted by and forms an adduct with said lactam;

recovering said adduct from said first distillation column;

passing said recovered adduct into a second distillation column;

subjecting said adduct to rectification in said second column so as to form a first fraction rich in said lactam and a second fraction rich in said at least one acid;

separating recovering said first and second fractions from said second distillation column; and recycling said first lactam-rich fraction to said first distillation column.

19. A method according to claim 18 wherein said lactam is a member of the following group: N-methyl pyrrolidone, N-isopropyl pyrrolidone and 2-pyrrolidone.

* * * * *